United States Patent
Fujii

(10) Patent No.: US 8,767,320 B2
(45) Date of Patent: Jul. 1, 2014

(54) ENDOSCOPE OPTICAL SYSTEM AND ENDOSCOPE

(75) Inventor: Hiroaki Fujii, Tokyo (JP)

(73) Assignee: Hoya Corporation, Tokyo (JP)

( * ) Notice: Subject to any disclaimer, the term of this patent is extended or adjusted under 35 U.S.C. 154(b) by 0 days.

(21) Appl. No.: 13/984,169

(22) PCT Filed: Feb. 7, 2012

(86) PCT No.: PCT/JP2012/000795
§ 371 (c)(1),
(2), (4) Date: Aug. 7, 2013

(87) PCT Pub. No.: WO2012/108177
PCT Pub. Date: Aug. 16, 2012

(65) Prior Publication Data
US 2013/0317299 A1 Nov. 28, 2013

(30) Foreign Application Priority Data
Feb. 10, 2011 (JP) .................. 2011-027091

(51) Int. Cl.
*G02B 21/02* (2006.01)
*G02B 13/04* (2006.01)
*G02B 9/34* (2006.01)
*G02B 23/24* (2006.01)

(52) U.S. Cl.
CPC .............. *G02B 23/243* (2013.01); *G02B 13/04* (2013.01); *G02B 9/34* (2013.01); *G02B 23/2423* (2013.01)
USPC ............................ 359/753; 359/660; 359/783

(58) Field of Classification Search
CPC .. G02B 23/243; G02B 23/2423; G02B 13/04; G02B 9/34
USPC .......................... 359/656–661, 749–753, 783
See application file for complete search history.

(56) References Cited

U.S. PATENT DOCUMENTS

| | | | |
|---|---|---|---|
| 5,175,650 A | 12/1992 | Takayama et al. | |
| 5,587,839 A | 12/1996 | Miyano et al. | |
| 6,327,101 B1 * | 12/2001 | Miyano | 359/691 |
| 2004/0240081 A1 | 12/2004 | Saito | |
| 2009/0086017 A1 | 4/2009 | Miyano | |

FOREIGN PATENT DOCUMENTS

| | | |
|---|---|---|
| JP | 02-293709 | 12/1990 |
| JP | 06-308381 | 11/1994 |

(Continued)

OTHER PUBLICATIONS

International Search Report dated May 15, 2012 with English language translation.

*Primary Examiner* — Scott J Sugarman
(74) *Attorney, Agent, or Firm* — Greenblum & Bernstein, P.L.C.

(57) ABSTRACT

An endoscope optical system, including a front group and a rear group arranged in this order from an object side such that an aperture stop is arranged between the front and rear groups, wherein the front group includes a negative lens and a positive lens arranged in this order from the object side, the rear group includes a positive lens and a cemented lens arranged in this order from the object side, and when f (unit: mm) denotes a focal length of an entire endoscope optical system, EX (unit: mm) denotes a distance (which takes a minus sign on the object side with respect to an image plane) from the image plane to an exit pupil, and $f_2$ (unit: mm) denotes a focal length of the rear group, the endoscope optical system satisfies conditions:

$$-10 < EX/f < -6 \qquad (1),$$

and $$1.15 < f_2/f < 1.35 \qquad (2).$$

7 Claims, 10 Drawing Sheets

(56) References Cited

FOREIGN PATENT DOCUMENTS

| JP | 08-122632 | 5/1996 |
| JP | 2004-61763 | 2/2004 |
| JP | 2004-354888 | 12/2004 |
| JP | 2007-249189 | 9/2007 |
| JP | 2009-80413 | 4/2009 |

\* cited by examiner

ENDOSCOPE OPTICAL SYSTEM AND ENDOSCOPE

TECHNICAL FIELD

The present invention relates to an endoscope optical system having optical performance suitable for observation of a body cavity, and an endoscope in which such an endoscope optical system is installed.

BACKGROUND ART

In a medical technology field, electronic endoscopes have been widely known and practically used as a device for observing a body cavity of a patient. Examples of an endoscope of this type are described in Japanese Patent Provisional Publications No. HEI 2-293709A (hereafter, referred to as patent document #1), No. HEI 6-308381A (hereafter, referred to as patent document #2), No. HEI 8-122632A (hereafter, referred to as patent document #3), No. 2004-61763A (hereafter, referred to as patent document #4), No. 2004-354888A (hereafter, referred to as patent document #5), and No. 2007-249189A (hereafter, referred to as patent document #6). The endoscope is designed to be thin so as to reduce burden on a patient during insertion into the patient's body cavity. In each of the patent documents #1 to #6, an exit pupil distance of the endoscope optical system is shortened so as to decrease the diameter of the endoscope optical system.

SUMMARY OF INVENTION

The endoscope optical system described in each of the patent documents #1 to #6 is designed on the assumption that the endoscope optical system is used for an image pick-up device having a small number of pixels. However, recently, an electronic scope in which an image pick-up device having a large number of pixels (e.g., a megapixel image pick-up device) is installed has been brought to practical use.

In the electronic scope in which the megapixel image pick-up device is installed, the size of each pixel is small and the photo acceptance efficiency is small. Therefore, when the endoscope optical system described in each of the patent documents #1 to #6 is employed in an endoscope, the shortage of the peripheral light amount by shading becomes large because the incident angle of a light ray proceeding to a peripheral part of the image pick-up device is large. Even for an image pick-up device on which a micro lens array is mounted, it is difficult to sufficiently suppress shading. There is a possibility that the shading can be sufficiently suppressed by enhancing accuracy of the micro lens array. However, in view of aspects of manufacturing technology and manufacturing cost, the strategy of suppressing the shading by enhancing the accuracy of the micro lens array cannot be easily employed.

The present invention is advantageous in that it provides an endoscope optical system suitable for suppressing shortage of the peripheral light amount caused by shading, and to provide an endoscope having such an optical system.

According to an aspect of the invention, there is provided an endoscope optical system, which includes a front group and a rear group. The front group and the rear group are arranged in this order from an object side such that an aperture stop is arranged between the front group and the rear group. The front group comprises a negative lens and a positive lens arranged in this order from the object side, and the rear group comprises a positive lens and a cemented lens arranged in this order from the object side. When f (unit: mm) denotes a focal length of an entire endoscope optical system, EX (unit: mm) denotes a distance (which takes a minus sign on the object side with respect to an image plane) from the image plane to an exit pupil, and $f_2$ (unit: mm) denotes a focal length of the rear group, the endoscope optical system satisfies conditions:

$$-10 < EX/f < -6 \quad (1),$$

and $$1.15 < f_2/f < 1.35 \quad (2).$$

By satisfying the conditions (1) and (2) simultaneously, it becomes possible to design an endoscope optical system having a wide field angle to suppress the size thereof to be suitable for mounting on an endoscope having a small diameter while securing optical performance required for observation of a fine structure in a body cavity. In particular, since the incident angle of light with respect to an imaging plane can be suppressed by securing the exit pupil distance EX, the shortage of the peripheral light amount by shading is small even when an image formed on an image pick-up device having a large number of pixels, such as a megapixel. Furthermore, by designing the endoscope optical system not to become a telecentric optical system while suppressing the incident angle with respect to the imaging plane, it becomes possible to suppress the diameter of the endoscope optical system to be a small diameter.

In order to provide an optical surface on a side close to the imaging plane and thereby to more suitably secure the exit pupil distance EX, the endoscope optical system may be configured such that when $f_c$ (unit: mm) denotes a focal length of the cemented lens, the endoscope optical system satisfies a condition:

$$2 < f_c/f_2 < 3.2 \quad (3).$$

In order to more suitably correct the aberrations, such as a coma and the chromatic aberration, the endoscope optical system may be configured such that when $f_1$ (unit: mm) denotes a focal length of the front group, the endoscope optical system satisfies a condition:

$$-2.5 < f_1/f < -1.2 \quad (4).$$

In order to more suitably secure the exit pupil distance EX, the endoscope optical system may be configured such that when $R_8$ (unit: mm) denotes a radius of curvature of an object side surface of the cemented lens and $R_{10}$ (unit: mm) denotes a radius of curvature of an image side surface of the cemented lens, the endoscope optical system satisfies a condition (5) or a condition (6) indicated below.

$$-0.5 < R_{10}/|R_8| <= 0 \quad (5)$$

$$|R_8|/R_{10} < -2 \quad (6)$$

In order to more suitably correct the aberrations, such as a coma and the astigmatism, the endoscope optical system may be configured such that the positive lens of the rear group is a positive meniscus lens having a concave surface facing the object side, and when $f_{21}$ (unit: mm) denotes a focal length of the positive lens of the rear group, and $R_6$ (unit: mm) denotes a radius of curvature of an object side surface of the positive lens of the rear group, the endoscope optical system satisfies conditions:

$$1.3 < f_{21}/f < 1.8 \quad (7),$$

and $$-1 < f/R_6 < -0.3 \quad (8).$$

According to another aspect of the invention, there is provided an endoscope, which includes a flexible insertion tube having one of the above described endoscope optical system provided at a tip part of the flexible insertion tube.

As described above, according to the invention, an endoscope optical system suitable for suppressing the shortage of the peripheral light amount caused by shading and an endoscope having such an endoscope optical system are provided.

DESCRIPTION OF EMBODIMENTS

Hereinafter, an endoscope optical system and an electronic scope having the endoscope optical system according to an embodiment of the present invention are described with reference to the accompanying drawings.

Figure 1:
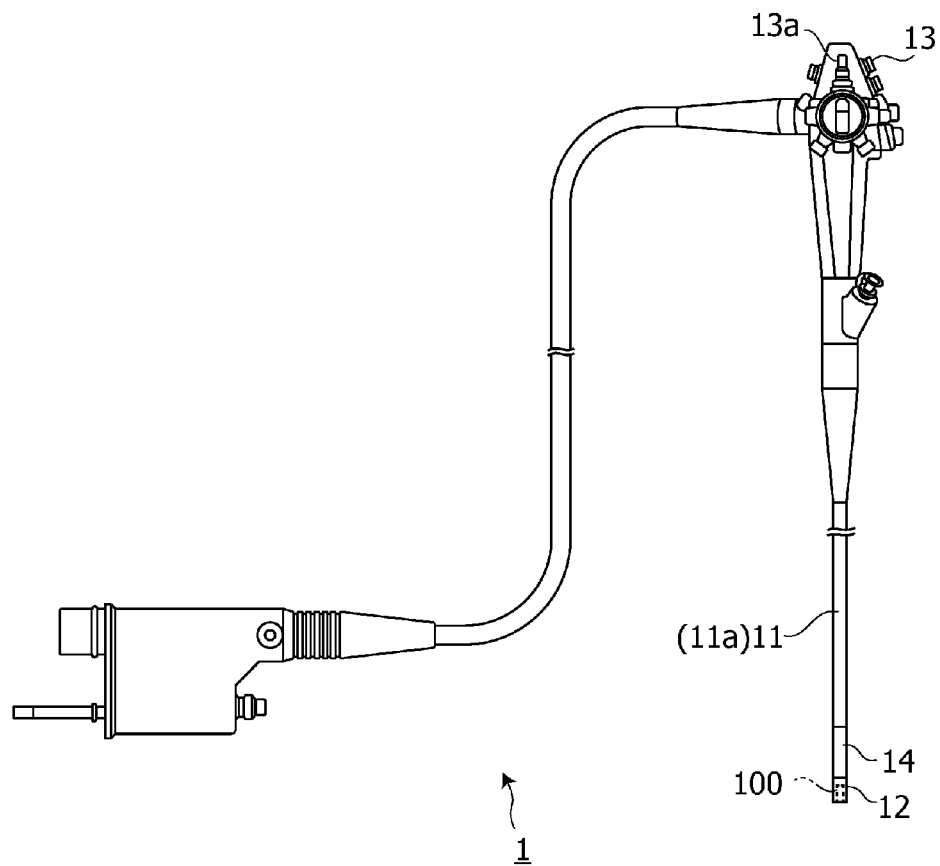
FIG. 1 illustrates an outer appearance of an electronic scope according to an embodiment of the invention.

FIG. 1 illustrates an outer appearance of an electronic scope 1 according to the embodiment. As shown in FIG. 1, the electronic scope 1 has a flexible insertion tube 11 (hereafter, simply referred to as a flexible tube 11) covered from the outside by a flexible sheath 11a. To a tip of the flexible tube 11, a tip part 12 which is covered from the outside by a resin housing having rigidity is connected. A bending part 14 provided at a connecting portion between the flexible tube 11 and the tip part 12 is configured to be able to bend freely through remote manipulation (specifically, rotational operation for a bending operation knob 13a) from an operation unit 13 connected to a proximal end of the flexible tube 11. This bending mechanism has a general configuration installed in a general electronic scope, and is configured to bend the bending part 14 by pulling an operation wire which moves in conjunction with the rotational operation for the bending operation knob 13a. By changing the direction of the tip part 12 in response to the bending movement by the above described operation, an imaging area of the electronic scope 1 moves.

In the resin housing of the tip part 12, an endoscope optical system 100 (indicated in a box shape in FIG. 1) is installed. In order to obtain image data of a subject in the imaging area, the endoscope optical system 100 causes reflected light from the subject to converge onto a photo acceptance surface of a solid state image pick-up device (not shown). As a solid state image pick-up device, a CCD (Charge Coupled Device) image sensor or a CMOS (Complementary Metal Oxide Semiconductor) image sensor can be cited, for example.

The electronic scope 1 according to the embodiment is designed to be targeted for observation of, for example, a lower digestive organ. Therefore, if the view angle of the endoscope optical system 100 is narrow, there is a concern that an affected area is overlooked. For this reason, the endoscope optical system 100 according to the embodiment is configured on the assumption that the view angle larger than that of a general digital still camera (e.g., the view angle larger than or equal to 120 degrees) is employed.

Figure 2:
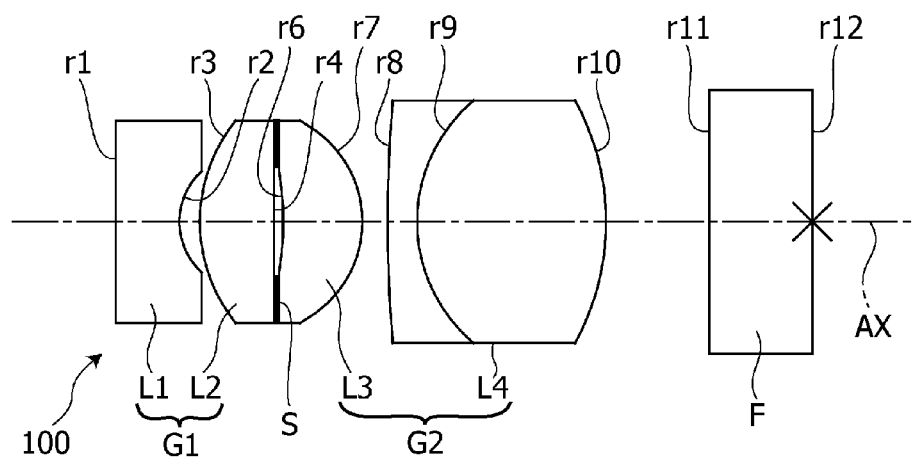
FIG. 2 is a cross sectional view of an endoscope optical system and optical components located on the downstream side of the endoscope optical system according to the embodiment (example 1) of the invention.

FIG. 2 is a cross sectional view of the endoscope optical system 100 according to example 1 (which is described in detail later) and optical components located on the downstream side of the endoscope optical system 100. Hereafter, the endoscope optical system 100 is explained in detail with reference to FIG. 2.

As shown in FIG. 2, the endoscope optical system 100 includes at least a front group G1 and a rear group G2 arranged in this order for from the object (subject) side. More specifically, an optical lens group arranged on the object side with respect to an aperture stop S constitutes the front group G1, and an optical lens group arranged on the image side with respect to the aperture stop S constitutes the rear group G2.

Each optical lens constituting the front and rear groups G1 and G2 is configured to be rotationally symmetric with respect to an optical axis AX of the endoscope optical system 100. On the rear side of the rear group G2, a filter unit F which covers the entire surface of the photo acceptance surface of the solid state image pick-up device is arranged. The filer unit F includes a plurality of layers, such as a color correction filter and a cover glass. In this specification and drawings, the filer unit F is illustrated as a single layer for the sake of simplicity.

It should be noted that the expression like "includes at least . . . " is used in the foregoing because, in another configuration example, the endoscope optical system may include another optical component within the scope of the technical concept of the invention. For example, a configuration where a flat plate not substantially contributing to the optical performance of the endoscope optical system is added to the endoscope optical system according to the invention or a configuration where an optical element is added to the endoscope optical system while maintaining the principal configuration and the advantages of the endoscope optical system according to the invention can be considered. For the same reason, in the following, the expression like "includes at least . . . " is used for explanation of the front group G1 and the rear group G2.

The front group G1 is a lens group having a negative power, and includes at least a negative lens L1 and a positive lens L2 arranged in this order from the object side.

The rear group G2 is a lens group having a positive power, and includes at least a positive lens L3 and a cemented lens L4 arranged in this order from the object side. The cemented lens L4 is formed by cementing together positive and negative lenses.

In the following, for each of the optical components, an object side surface is referred to as a first surface and an image side surface is referred to as a second surface for the sake of simplicity. The aperture stop S may be a plate-like member having a predetermined circular aperture centering on the optical axis AX, or a light-shielding film coated on a portion other than a predetermined circular area centering on the optical axis AX on a lens surface nearest to the aperture stop S in the front group G1 (i.e., a second surface r4 of the positive lens L2 in the configuration of FIG. 2). The thickness of the aperture stop S is considerably small in comparison with the thickness of each of the optical lenses constituting the endoscope optical system 100, and can be neglected in regard to calculation of the optical performance of the endoscope optical system 100. Therefore, in this specification, the explanation is made assuming that the thickness of the aperture stop S is zero.

When f (unit: mm) denotes the focal length of the entire endoscope optical system 100, EX (unit: mm) denotes an exit pupil distance from the image plane to the exit pupil of the endoscope optical system 100, and $f_2$ (unit: mm) denotes the focal length of the rear group G2, the endoscope optical system 100 is configured to satisfy conditions:

$$-10 < EX/f < -6 \qquad (1),$$

and $$1.15 < f_2/f < 1.35 \qquad (2).$$

The image plane corresponds to the light acceptance surface of the solid state image pick-up device, and is positioned substantially at the same position as the position of a second surface r12 of the filer unit F. The exit pupil distance EX extends to the object side with respect to the image plane, and takes a negative sign.

When the intermediate term of the condition (1) gets larger than the upper limit of the condition (1), the incident angle of light with respect to the light acceptance surface of the solid state image pick-up device becomes large, and therefore the shortage of the peripheral light amount by shading becomes large. In particular, since an image pick-up device having a large number of pixels, such as a megapixel, has a small pixel size and a low degree of light acceptance efficiency (it should be noted that since the image pick-up device is installed in a tip part of a thin endoscope, the size of the image pick-up device is limited and therefore the size of each pixel is small), the effect of suppressing the shading by a micro lens array is small and the shortage of the peripheral light amount is large. Since the solid state image pick-up device is a fine chip, in this embodiment it is assumed that the position of the photo acceptance surface of the solid state image pick-up device is substantially the same as the position of the micro lens array in the optical axis direction.

When the intermediate term of the condition (1) gets smaller than the lower limit of the condition (1), it becomes necessary to increase the lens diameter of the cemented lens L4 so as to secure the required optical performance of the electronic scope 1 having the wide field angle (e.g., the field angle larger than or equal to 120 degrees) for observing a fine structure in a body cavity. In this case, it becomes difficult to install the endoscope optical system in the tip part 12 having a small diameter.

In general, in an optical system configured such that a rear group having a positive power is arranged close to an aperture stop, the front side focal position of the rear group is located on the object side with respect to an aperture stop. Therefore, when the power of the rear group becomes weak (i.e., when the focal length becomes long), the positive magnification becomes small, and the exit pupil distance becomes short. When the intermediate term of the condition (2) gets larger than the upper limit of the condition (2), the exit pupil distance EX becomes short because the power of the rear group G2 is small and the positive magnification is small, and in this case the shortage of the peripheral light amount by shading becomes large.

When the intermediate term of the condition (2) gets smaller than the lower limit of the condition (2), it becomes necessary to increase the lens diameter of the cemented lens L4 to secure the required optical performance for observation of a body cavity. Since the curvature of field (in particular, the curvature of the meridional image plane) is caused largely in accordance with increase of the diameter of the cemented lens L4, it is difficult to correct the astigmatism for the entire image height.

When the conditions (1) and (2) are satisfied simultaneously, it becomes possible to design the endoscope optical system 100 having the wide filed angle such that the endoscope optical system 100 has the size suitable for installation in the tip part 12 having the small diameter while securing the optical performance required for observation for a fine structure of a body cavity. In particular, since the incident angle of light with respect to an imaging plane can be suppressed by securing the exit pupil distance EX, the shortage of the peripheral light amount by shading is small even when the image is formed on the image pick-up device having a large number of pixels, such as a megapixel. Furthermore, by designing the endoscope optical system 100 so as not to be formed as a telecentric optical system while suppressing the incident angle of light with respect to the imaging plane, the diameter of the endoscope optical system 100 can be decreased.

In order to more suitably secure the exit pupil distance EX by giving power to an optical surface on the side close to the imaging plane, the endoscope optical system 100 is configured to satisfy a condition:

$$2 < f_c/f_2 < 3.2 \quad (3)$$

where $f_c$ (unit: mm) denotes a focal length of the cemented lens L4.

In general, in an optical system where a rear group having a positive power is arranged close to an aperture stop, when the power of a lens arranged nearest to the image side in the rear group becomes weak, the front side principal point of the rear group approaches to the object side (i.e., on the side closer to the aperture stop) and the positive magnification becomes small, and thereby the exit pupil distance becomes short. When the intermediate term of the condition (3) gets larger than the upper limit of the condition (3), the exit pupil distance EX becomes short because the power of the cemented lens L4 is weak and the positive magnification is small, and thereby the shortage of the peripheral light amount by shading becomes large.

When the intermediate term of the condition (3) gets smaller than the lower limit of the condition (3), it becomes difficult for the cemented lens L4 having the size fitted in the tip part 12 (i.e., the tip part 12 having a small size) to secure the peripheral part thickness. Furthermore, since the power of the cemented lens L4 is too strong, deterioration of the aberration (in particular, occurrence of the astigmatism caused by the curvature of the meridional image plane) by an installation error (i.e., decentering) is large.

In order to more suitably correct the aberrations including a coma and a chromatic aberration, the endoscope optical system 100 is configured to satisfy a condition:

$$-2.5 < f_1/f < -1.2 \quad (4)$$

where $f_1$ (unit: mm) denotes the focal length of the front group G1.

When the intermediate term of the condition (4) gets larger than the upper limit of the condition (4), the negative power of the front group G1 is too strong, and therefore it becomes difficult to suitably correct the aberrations including a coma and the chromatic aberration when a designer tries to design the endoscope optical system to have a wide filed angle required for observation of a body cavity. Furthermore, since in this case it is necessary to set the magnification of the rear group G2 to be high, it becomes difficult to suppress change of the magnification of the rear group G2 due to an error of an interval between the front and rear groups G1 and G2 during assembling. Furthermore, since the change of the filed angle due to change of the magnification of the rear group G2 becomes also large, it becomes difficult to assure the stable field angle which satisfies the requirements.

When the intermediate term of the condition (4) gets smaller than the lower limit of the condition (4), it becomes difficult to design the endoscope optical system 100 to suppress the outer diameter of each optical lens, and therefore the endoscope optical system 100 becomes unsuitable for installation in the tip part 12 having a small diameter. Furthermore, since in this case it is necessary to set the magnification of the front group G1 to be high, inclination of the image plane defined when the front group G1 is installed in a state where the front group G1 is decenterred with respect to the optical axis AX becomes large, and deterioration of image quality becomes easy to occur in the peripheral part of the observation field. It should be noted that the inclination of the image plane means a phenomenon where the curvature of field ideally remaining symmetrically with respect to the optical axis remains asymmetrically with respect to the optical axis depending on the decentering amount and the decentering direction of an imaging lens caused during assembling.

In order to secure the exit pupil distance EX more suitably, the endoscope optical system 100 is configured to satisfy a condition (5) or a condition (6):

$$-0.5 < R_{10}/|R_8| <= 0 \quad (5)$$

$$|R_8|/R_{10} < -2 \quad (6)$$

where $R_8$ (unit: mm) denotes a radius of curvature of the first surface r8 of the cemented lens L4 and $R_{10}$ (unit: mm) denotes a radius of curvature of the second surface r10 of the cemented lens L4.

When the intermediate term of the condition (5) gets larger than the upper limit of the condition (5), the second surface r10 located nearest to the image side in the rear group G2 becomes a concave surface and the exit pupil distance EX becomes short, and therefore the shortage of the peripheral light amount by shading becomes large.

When the intermediate term of the condition (5) gets smaller than the lower limit of the condition (5) or the intermediate term of the condition (6) gets larger than the upper limit of the condition (6), the exit pupil distance EX becomes short because the power of the cemented lens L4 is weak and the positive magnification is small, and therefore the shortage of the peripheral light amount by shading becomes large.

In order to more suitably correct the aberrations such as a coma and the astigmatism, when the positive lens L3 is a meniscus lens having a concave surface on the object side as shown in FIG. 2, $f_{21}$ (unit: mm) denotes the focal length of the positive lens L3, and $R_6$ (unit: mm) denotes the radius of curvature of the first surface r6 of the positive lens L3, the endoscope optical system 100 is configured to simultaneously satisfy the following conditions:

$$1.3 < f_{21}/f < 1.8 \quad (7),$$

and $$-1 < f/R_6 < -0.3 \quad (8)$$

When the intermediate term of the condition (7) gets larger than the upper limit of the condition (7), the power of the positive lens L3 is weak and the coma increases. Specifically, in order to secure the positive power, the radius of curvature of the first surface r6 (a concave surface) decreases extremely in place of a second surface r7 (a convex surface) of the positive lens L3 whose radius of curvature cannot be set to be large. In this case, the coma increases. In order to maintain the power of the rear group G2, the power of the cemented lens L4 needs to be set to be large. In this case, there is a concern with respect to deterioration of the aberration performance due to an assembling decentering error (in particular, occurrence of astigmatism due to curvature of the meridional image plane).

When the intermediate term of the condition (7) gets smaller than the lower limit of the condition (7), it becomes impossible to obtain the suitable aberration performance because the power of the positive lens L3 is too strong. Specifically, the spherical aberration largely occurs in accordance with increase of the power of the positive lens L3, and the curvature of field occurs largely due to increase of Petzval sum, and the astigmatism due to an assembling decentering error increases.

When the intermediate term of the condition (8) gets larger than the upper limit of the condition (8), it becomes difficult to correct the astigmatism because the radius of curvature of the first surface r6 (a concave surface) of the positive lens L3 is large.

When the intermediate term of the condition (8) gets smaller than the lower limit of the condition (8), the power of the positive lens L3 is weak and the coma increases because the radius of curvature of the first surface r6 (a concave surface) of the positive lens L3 is small.

In the following, seven concrete numeric examples (examples 1 to 7) of the endoscope optical system 100 and two comparative examples (comparative examples 1 and 2) to be compared with the examples 1 to 7 are explained. The endoscope optical system of each of the examples 1 to 7 and the comparative examples 1 and 2 is arranged in the tip part 12 of the electronic scope 1 shown in FIG. 1.

Example 1

As described above, the endoscope optical system 100 according to the example 1 has the configuration shown in FIG. 2.

Table 1 shows the numeric configuration (design values) of the endoscope optical system 100 (and optical components located on the rear side thereof) according to the example 1. In Table 1, surface No. corresponds to the reference symbol m (n: integer) assigned to each surface in FIG. 2, excepting the surface No. 5 of the aperture stop S. In Table 1, "R" (unit: mm) denotes a radius of curvature of each lens surface, "D" (unit: mm) denotes a thickness of an optical component or an interval between optical components, N(d) denotes a refractive index at the d-line (wavelength of 588 nm), and, vd is Abbe number at the d-line. Table 2 shows the specifications of the endoscope optical system 100. The specifications include an effective F number, the optical magnification, the half field angle (unit: degree), the image height (unit: mm), the back focus BF (unit: mm), the overall length (unit: mm) of the endoscope optical system 100, the focal length f (unit: mm) of the entire optical system, the exit pupil distance EX (unit: mm), the focal length $f_1$ (unit: mm) of the front group G1, the focal length $f_2$ (unit: mm) of the rear group G2, the focal length $f_{21}$ (unit: mm) of the positive lens L3 and the focal length $f_c$ (unit: mm) of the cemented lens L4.

TABLE 1

| Surface No. | R | D | N(d) | vd |
|---|---|---|---|---|
| 1 | INFINITY | 0.619 | 1.88300 | 40.8 |
| 2 | 0.682 | 0.199 | | |
| 3 | 1.610 | 0.724 | 1.84666 | 23.8 |
| 4 | INFINITY | 0.000 | | |
| 5(aperture stop) | INFINITY | 0.086 | | |
| 6 | −3.174 | 0.769 | 1.88300 | 40.8 |
| 7 | −1.130 | 0.246 | | |
| 8 | 14.325 | 0.286 | 1.92286 | 18.9 |
| 9 | 1.585 | 1.838 | 1.77250 | 49.6 |
| 10 | −2.530 | 1.002 | | |
| 11 | INFINITY | 1.000 | 1.51680 | 64.2 |
| 12 | INFINITY | — | | |

TABLE 2

| | |
|---|---|
| F number | 5.700 |
| Magnification | −0.086 |
| Half Field Angle | 72.200 |
| Image Height | 1.210 |
| Back Focus BF | 0.000 |
| Overall Length of Lens | 6.770 |
| Focal Length f | 1.179 |
| Exit Pupil Distance EX | −8.090 |
| Focal Length $f_1$ of Front Group G1 | −1.579 |
| Focal Length $f_2$ of Rear Group G2 | 1.523 |

TABLE 2-continued

| | |
|---|---|
| Focal Length $f_{21}$ of Positive Lens L3 | 1.689 |
| Focal Length $f_c$ of Cemented Lens L4 | 3.544 |

Figure 3:
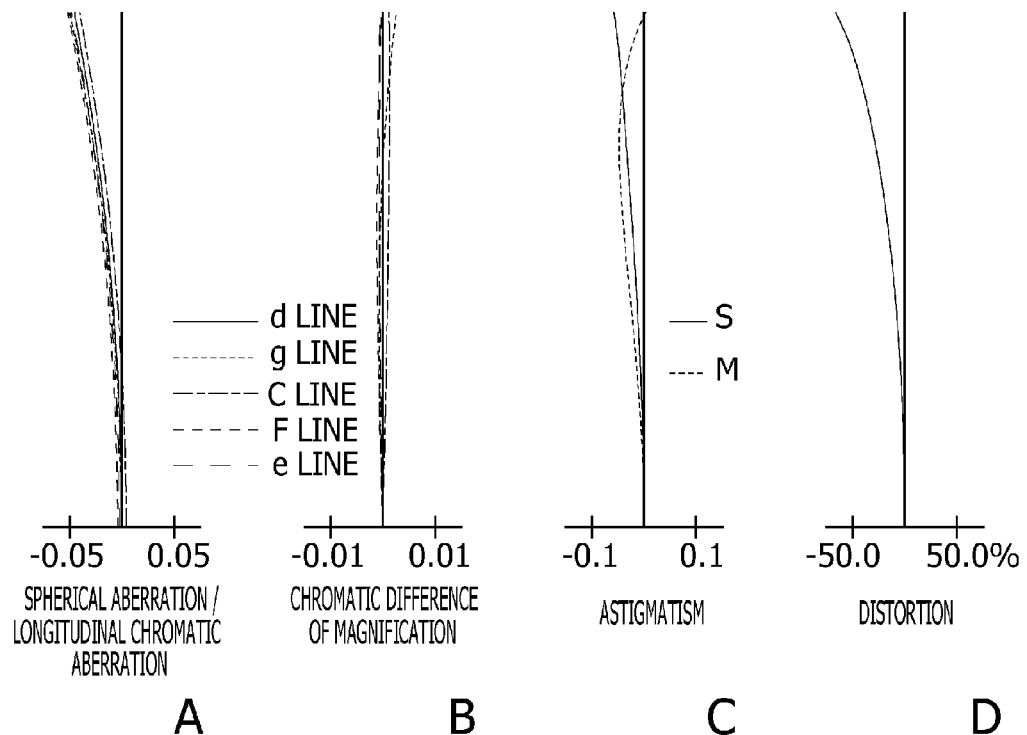
FIGS. 3A to 3D are graphs illustrating the aberrations of the endoscope optical system according to the example 1 of the invention.

FIGS. 3A to 3D are aberration diagrams of the endoscope optical system 100 according to the example 1. Specifically, FIG. 3A is a graph illustrating the spherical aberration and the longitudinal chromatic aberration at each of d-line (588 nm), g-line (436 nm), C-line (656 nm), F-line (486 nm) and e-line (546 nm). FIG. 3B is a graph illustrating the chromatic difference of magnification at each of d-line, g-line, C-line, F-line and e-line. In each of FIGS. 3A and 3B, a curve indicated by a solid line represents the aberration at d-line, a curve indicated by a dotted line represents the aberration at g-line, a curve indicated by a chain line represents the aberration at C-line, a curve indicated by a short dashed line represents the aberration at F-line, a curve indicated by a long dashed line represents the aberration at e-line. FIG. 3C shows the astigmatism. In FIG. 3C, a curve indicated by a solid line represents a sagittal component and a curve indicated by a dotted line represents a meridional component. FIG. 3D shows the distortion. In each of FIGS. 3A to 3C, the vertical axis represents the image height, and the horizontal axis represents the aberration amount. In FIG. 3D, the vertical axis represents the image height, and the horizontal axis represents the distortion. The definitions of the symbols and explanations with respect to the tables and drawings in the example 1 also apply to tables and drawings of the following examples and the comparative examples.

Example 2

Figure 4:
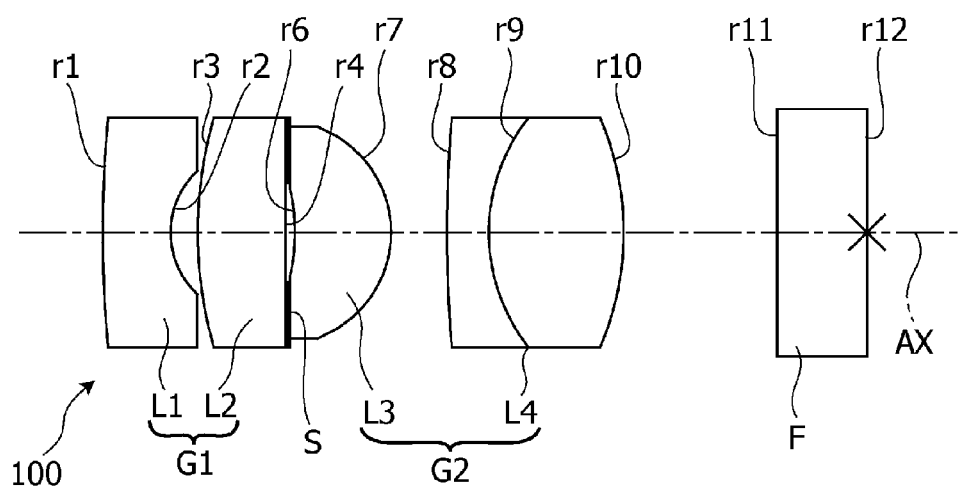
FIG. 4 is a cross sectional view of an endoscope optical system and optical components located on the downstream side of the endoscope optical system according to example 2 of the invention.
Figure 5:
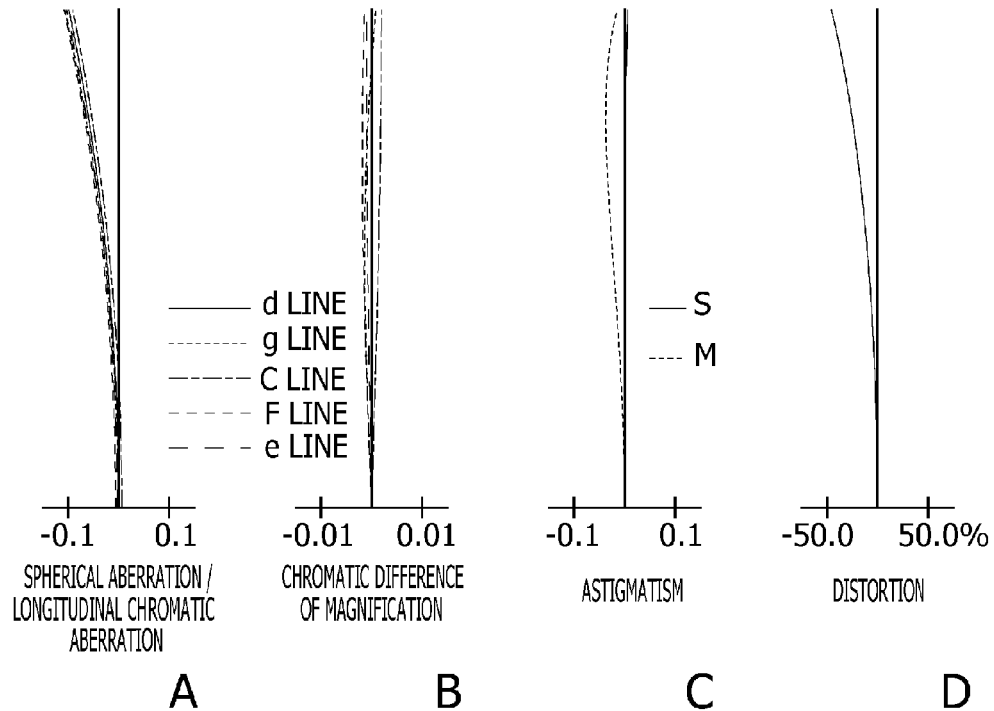
FIGS. 5A to 5D are graphs illustrating the aberrations of the endoscope optical system according to the example 2 of the invention.

FIG. 4 is a cross sectional view illustrating the arrangement of the optical components including the endoscope optical system 100 according to the example 2. As shown in FIG. 4, the endoscope optical system 100 according to the example 2 has the same number of optical components as that of the endoscope optical system 100 according to the example 1. FIGS. 5A to 5D are aberration diagrams (the spherical aberration, the longitudinal chromatic aberration, the chromatic difference of magnification, the astigmatism and the distortion) of the endoscope optical system 100 according to the example 2. Table 3 shows the numeric configuration of the optical components including the endoscope optical system 100 according to the example 2. Table 4 shows the specifications of the endoscope optical system 100 according to the example 2.

TABLE 3

| Surface No. | R | D | N(d) | vd |
|---|---|---|---|---|
| 1 | 13.968 | 0.757 | 1.88300 | 40.8 |
| 2 | 0.975 | 0.303 | | |
| 3 | 4.838 | 0.977 | 1.84666 | 23.8 |
| 4 | INFINITY | 0.000 | | |
| 5(aperture stop) | INFINITY | 0.105 | | |
| 6 | −2.354 | 1.072 | 1.88300 | 40.8 |
| 7 | −1.290 | 0.621 | | |
| 8 | 15.582 | 0.466 | 1.92286 | 18.9 |
| 9 | 2.140 | 1.503 | 1.77250 | 49.6 |
| 10 | −3.338 | 1.710 | | |
| 11 | INFINITY | 1.000 | 1.51680 | 64.2 |
| 12 | INFINITY | — | | |

TABLE 4

| | |
|---|---|
| F number | 5.6000 |
| Magnification | −0.077 |
| Half Field Angle | 60.900 |
| Image Height | 1.320 |
| Back Focus BF | 0.000 |
| Overall Length of Lens | 8.510 |
| Focal Length f | 1.367 |
| Exit Pupil Distance EX | −10.754 |
| Focal Length $f_1$ of Front Group G1 | −1.653 |
| Focal Length $f_2$ of Rear Group G2 | 1.813 |
| Focal Length $f_{21}$ of Positive Lens L3 | 2.194 |
| Focal Length $f_c$ of Cemented Lens L4 | 4.544 |

Example 3

Figure 6:
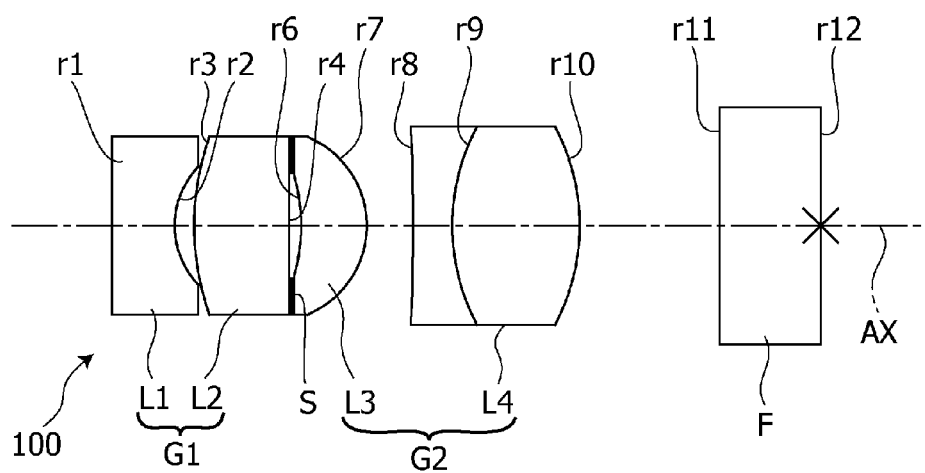
FIG. 6 is a cross sectional view of an endoscope optical system and optical components located on the downstream side of the endoscope optical system according to example 3 of the invention.
Figure 7:
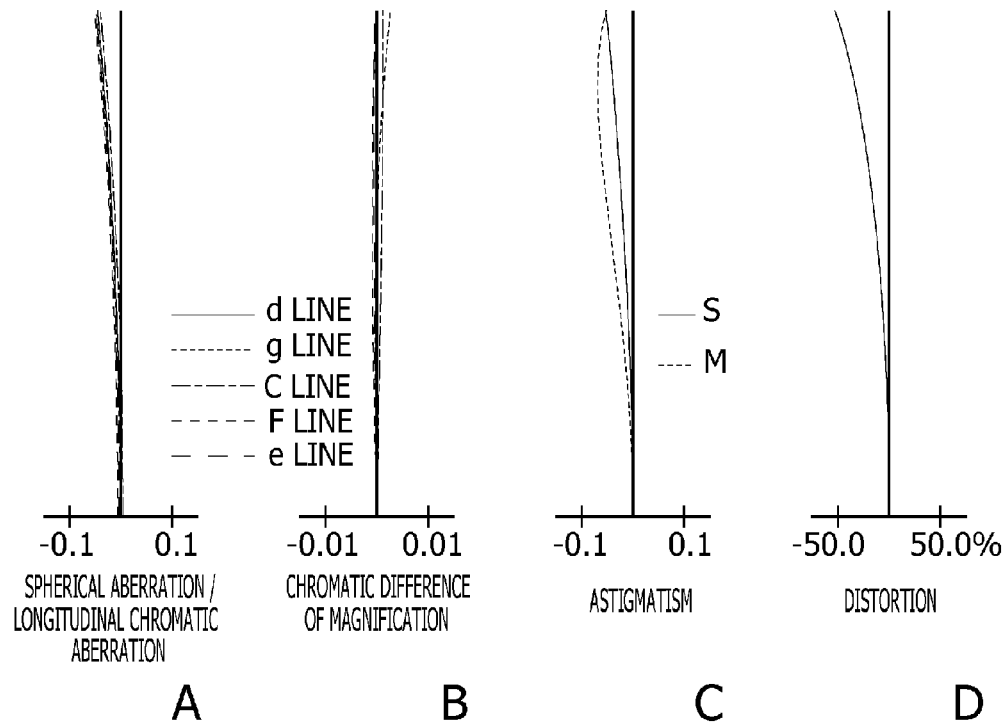
FIGS. 7A to 7D are graphs illustrating the aberrations of the endoscope optical system according to the example 3 of the invention.

FIG. 6 is a cross sectional view illustrating the arrangement of the optical components including the endoscope optical system 100 according to the example 3. As shown in FIG. 6, the endoscope optical system 100 according to the example 3 has the same number of optical components as that of the endoscope optical system 100 according to the example 1. FIGS. 7A to 7D are aberration diagrams (the spherical aberration, the longitudinal chromatic aberration, the chromatic difference of magnification, the astigmatism and the distortion) of the endoscope optical system 100 according to the example 3. Table 5 shows the numeric configuration of the optical components including the endoscope optical system 100 according to the example 3. Table 6 shows the specifications of the endoscope optical system 100 according to the example 3.

TABLE 5

| Surface No. | R | D | N(d) | vd |
|---|---|---|---|---|
| 1 | INFINITY | 0.623 | 1.88300 | 40.8 |
| 2 | 0.877 | 0.195 | | |
| 3 | 2.735 | 0.974 | 1.84666 | 23.8 |
| 4 | INFINITY | 0.000 | | |
| 5(aperture stop) | INFINITY | 0.088 | | |
| 6 | −1.851 | 0.653 | 1.88300 | 40.8 |
| 7 | −0.983 | 0.458 | | |
| 8 | −23.602 | 0.390 | 1.92286 | 18.9 |
| 9 | 2.159 | 1.266 | 1.77250 | 49.6 |
| 10 | −2.159 | 1.392 | | |
| 11 | INFINITY | 1.000 | 1.51680 | 64.2 |
| 12 | INFINITY | — | | |

TABLE 6

| | |
|---|---|
| F number | 8.500 |
| Magnification | −0.132 |
| Half Field Angle | 64.900 |
| Image Height | 1.170 |
| Back Focus BF | 0.000 |
| Overall Length of Lens | 7.040 |
| Focal Length f | 1.195 |
| Exit Pupil Distance EX | −8.159 |
| Focal Length $f_1$ of Front Group G1 | −1.570 |
| Focal Length $f_2$ of Rear Group G2 | 1.559 |
| Focal Length $f_{21}$ of Positive Lens L3 | 1.755 |
| Focal Length $f_c$ of Cemented Lens L4 | 3.580 |

Example 4

Figure 8:
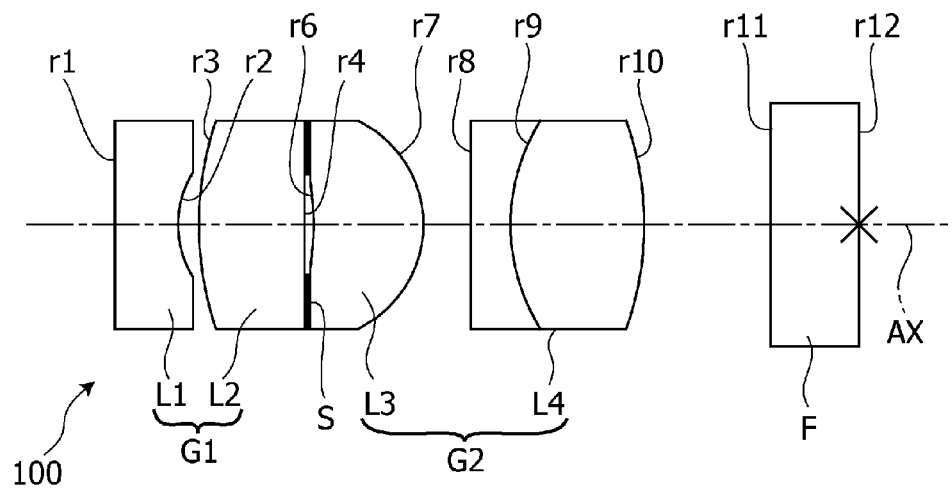
FIG. 8 is a cross sectional view of an endoscope optical system and optical components located on the downstream side of the endoscope optical system according to example 4 of the invention.
Figure 9:
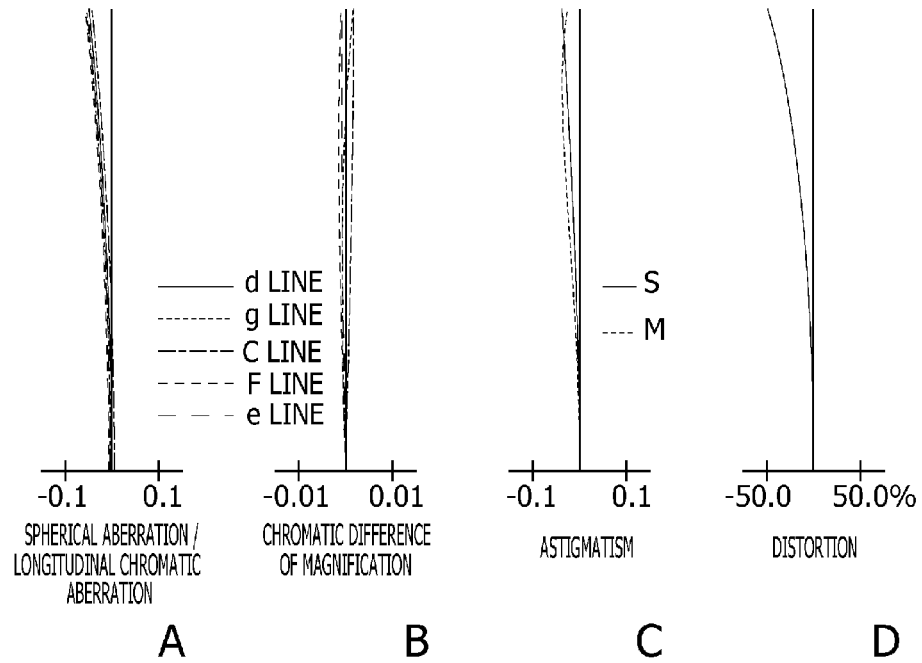
FIGS. 9A to 9D are graphs illustrating the aberrations of the endoscope optical system according to the example 4 of the invention.

FIG. 8 is a cross sectional view illustrating the arrangement of the optical components including the endoscope optical system 100 according to the example 4. As shown in FIG. 8, the endoscope optical system 100 according to the example 4 has the same number of optical components as that of the endoscope optical system 100 according to the example 1. FIGS. 9A to 9D are aberration diagrams (the spherical aberration, the longitudinal chromatic aberration, the chromatic difference of magnification, the astigmatism and the distortion) of the endoscope optical system 100 according to the example 4. Table 7 shows the numeric configuration of the optical components including the endoscope optical system 100 according to the example 4. Table 8 shows the specifications of the endoscope optical system 100 according to the example 4.

TABLE 7

| Surface No. | R | D | N(d) | vd |
|---|---|---|---|---|
| 1 | INFINITY | 0.717 | 1.88300 | 40.8 |
| 2 | 1.174 | 0.235 | | |
| 3 | 3.842 | 1.198 | 1.84666 | 23.8 |
| 4 | INFINITY | 0.000 | | |
| 5(aperture stop) | INFINITY | 0.101 | | |
| 6 | −3.119 | 1.243 | 1.88300 | 40.8 |
| 7 | −1.344 | 0.538 | | |
| 8 | INFINITY | 0.448 | 1.92286 | 18.9 |
| 9 | 2.304 | 1.512 | 1.81600 | 46.6 |
| 10 | −3.648 | 1.432 | | |
| 11 | INFINITY | 1.000 | 1.51680 | 64.2 |
| 12 | INFINITY | — | | |

TABLE 8

| | |
|---|---|
| F number | 8.100 |
| Magnification | −0.080 |
| Half Field Angle | 62.200 |
| Image Height | 1.300 |
| Back Focus BF | 0.000 |
| Overall Length of Lens | 8.420 |
| Focal Length f | 1.370 |
| Exit Pupil Distance EX | −10.312 |
| Focal Length $f_1$ of Front Group G1 | −2.029 |
| Focal Length $f_2$ of Rear Group G2 | 1.806 |
| Focal Length $f_{21}$ of Positive Lens L3 | 2.013 |
| Focal Length $f_c$ of Cemented Lens L4 | 5.378 |

Example 5

Figure 10:
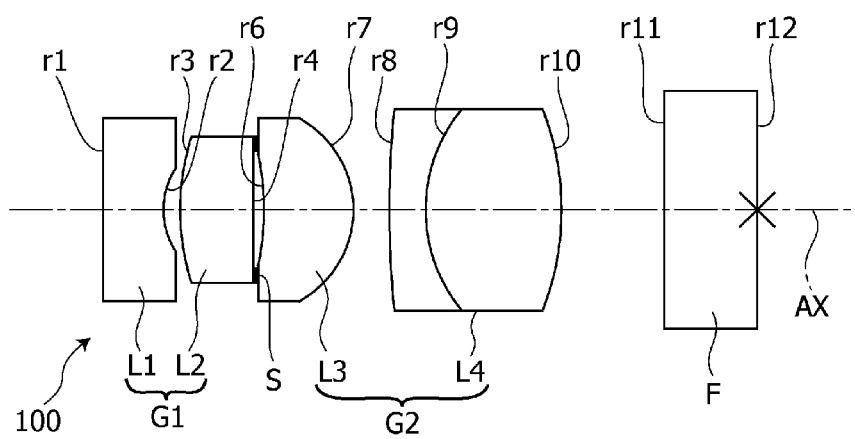
FIG. 10 is a cross sectional view of an endoscope optical system and optical components located on the downstream side of the endoscope optical system according to example 5 of the invention.
Figure 11:
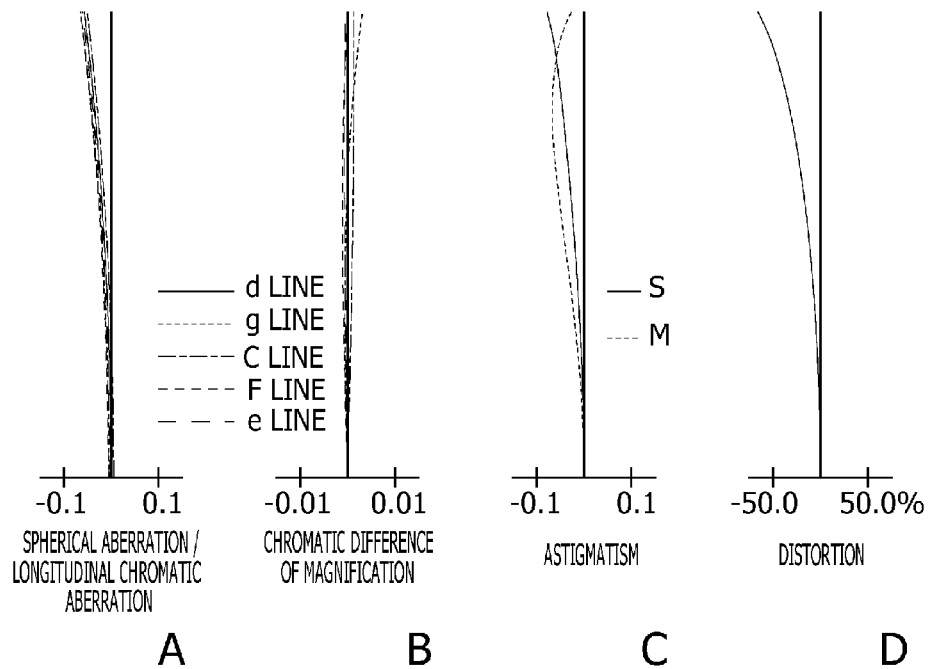
FIGS. 11A to 11D are graphs illustrating the aberrations of the endoscope optical system according to the example 5 of the invention.

FIG. 10 is a cross sectional view illustrating the arrangement of the optical components including the endoscope optical system 100 according to the example 5. As shown in FIG. 10, the endoscope optical system 100 according to the example 5 has the same number of optical components as that of the endoscope optical system 100 according to the example 1. FIGS. 11A to 11D are aberration diagrams (the spherical aberration, the longitudinal chromatic aberration, the chromatic difference of magnification, the astigmatism and the distortion) of the endoscope optical system 100 according to the example 5. Table 9 shows the numeric configuration of the optical components including the endoscope optical system 100 according to the example 5. Table 10 shows the specifications of the endoscope optical system 100 according to the example 5.

TABLE 9

| Surface No. | R | D | N(d) | vd |
|---|---|---|---|---|
| 1 | INFINITY | 0.652 | 1.88300 | 40.8 |
| 2 | 0.864 | 0.178 | | |
| 3 | 2.650 | 0.814 | 1.84666 | 23.8 |

TABLE 9-continued

| Surface No. | R | D | N(d) | νd |
|---|---|---|---|---|
| 4 | INFINITY | 0.000 | | |
| 5(aperture stop) | INFINITY | 0.088 | | |
| 6 | −2.973 | 0.963 | 1.88300 | 40.8 |
| 7 | −1.152 | 0.385 | | |
| 8 | 11.676 | 0.389 | 1.92286 | 18.9 |
| 9 | 1.752 | 1.460 | 1.77250 | 49.6 |
| 10 | −3.066 | 1.103 | | |
| 11 | INFINITY | 1.000 | 1.51680 | 64.2 |
| 12 | INFINITY | — | | |

TABLE 10

| | |
|---|---|
| F number | 6.000 |
| Magnification | −0.129 |
| Half Field Angle | 72.400 |
| Image Height | 1.240 |
| Back Focus BF | 0.000 |
| Overall Length of Lens | 7.030 |
| Focal Length f | 1.192 |
| Exit Pupil Distance EX | −8.129 |
| Focal Length $f_1$ of Front Group G1 | −1.552 |
| Focal Length $f_2$ of Rear Group G2 | 1.497 |
| Focal Length $f_{21}$ of Positive Lens L3 | 1.707 |
| Focal Length $f_c$ of Cemented Lens L4 | 4.105 |

Example 6

Figure 12:
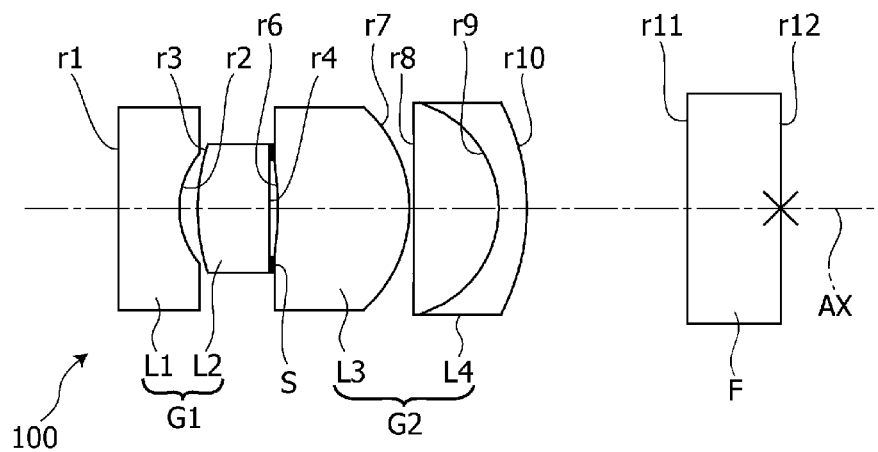
FIG. 12 is a cross sectional view of an endoscope optical system and optical components located on the downstream side of the endoscope optical system according to example 6 of the invention.
Figure 13:
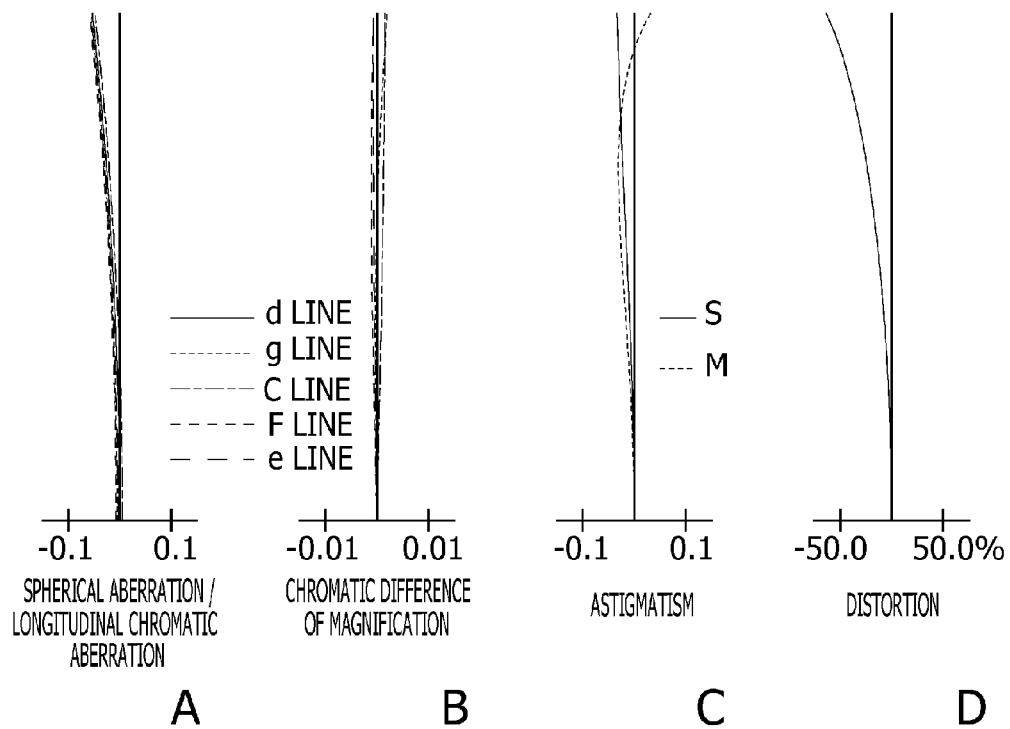
FIGS. 13A to 13D are graphs illustrating the aberrations of the endoscope optical system according to the example 6 of the invention.

FIG. 12 is a cross sectional view illustrating the arrangement of the optical components including the endoscope optical system 100 according to the example 6. As shown in FIG. 12, the endoscope optical system 100 according to the example 6 has the same number of optical components as that of the endoscope optical system 100 according to the example 1. FIGS. 13A to 13D are aberration diagrams (the spherical aberration, the longitudinal chromatic aberration, the chromatic difference of magnification, the astigmatism and the distortion) of the endoscope optical system 100 according to the example 6. Table 11 shows the numeric configuration of the optical components including the endoscope optical system 100 according to the example 6. Table 12 shows the specifications of the endoscope optical system 100 according to the example 6.

TABLE 11

| Surface No. | R | D | N(d) | νd |
|---|---|---|---|---|
| 1 | INFINITY | 0.650 | 1.88300 | 40.8 |
| 2 | 0.937 | 0.196 | | |
| 3 | 2.301 | 0.764 | 1.84666 | 23.8 |
| 4 | INFINITY | 0.000 | | |
| 5(aperture stop) | INFINITY | 0.090 | | |
| 6 | −3.720 | 1.407 | 1.88300 | 40.8 |
| 7 | −1.480 | 0.050 | | |
| 8 | −75.371 | 0.903 | 1.77250 | 49.6 |
| 9 | −1.206 | 0.300 | 1.92286 | 18.9 |
| 10 | −2.534 | 1.708 | | |
| 11 | INFINITY | 1.000 | 1.51680 | 64.2 |
| 12 | INFINITY | — | | |

TABLE 12

| | |
|---|---|
| F number | 4.800 |
| Magnification | −0.065 |
| Half Field Angle | 70.300 |

TABLE 12-continued

| | |
|---|---|
| Image Height | 1.250 |
| Back Focus BF | 0.000 |
| Overall Length of Lens | 7.070 |
| Focal Length f | 1.239 |
| Exit Pupil Distance EX | −8.322 |
| Focal Length $f_1$ of Front Group G1 | −1.976 |
| Focal Length $f_2$ of Rear Group G2 | 1.527 |
| Focal Length $f_{21}$ of Positive Lens L3 | 2.151 |
| Focal Length $f_c$ of Cemented Lens L4 | 4.198 |

Example 7

Figure 14:
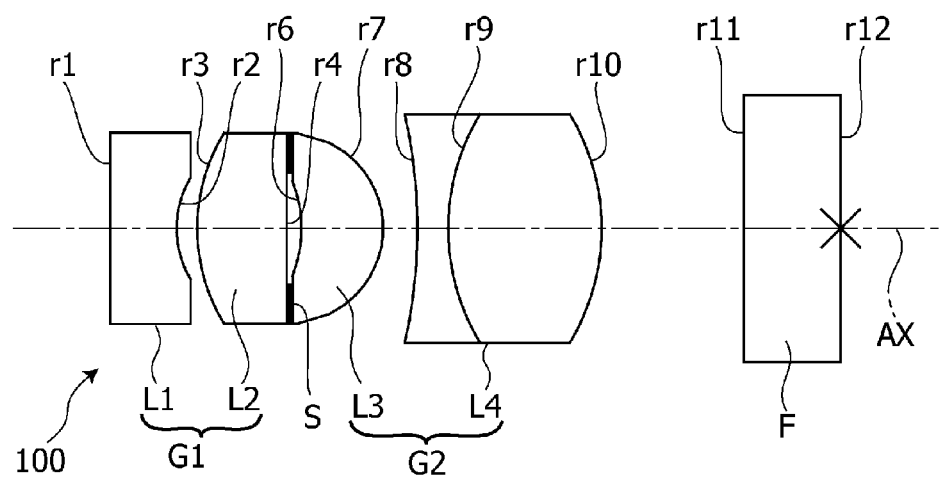
FIG. 14 is a cross sectional view of an endoscope optical system and optical components located on the downstream side of the endoscope optical system according to example 7 of the invention.
Figure 15:
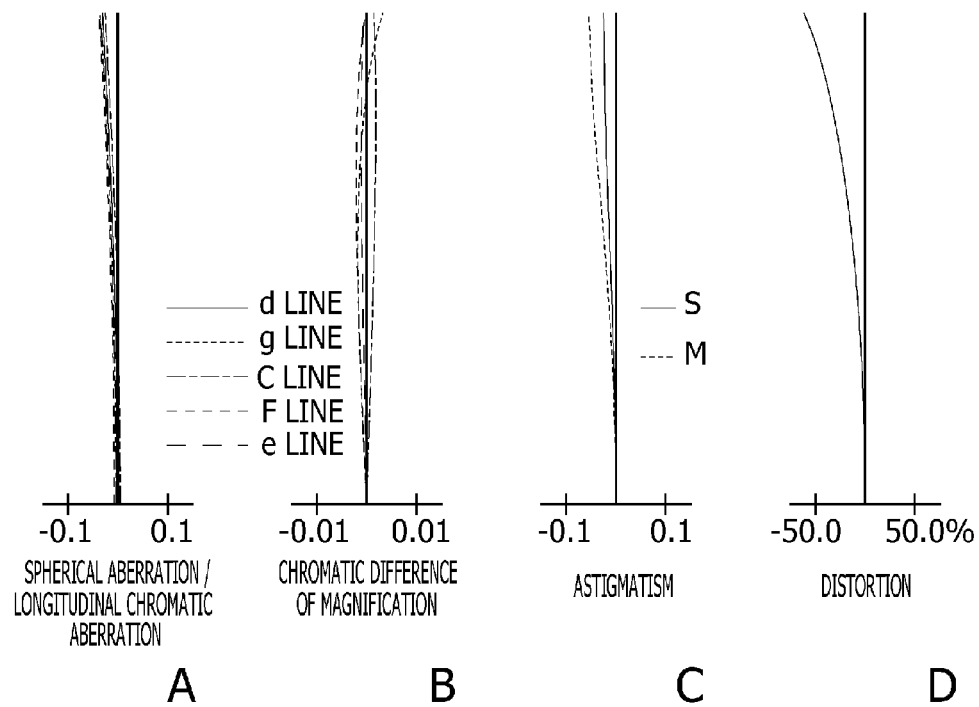
FIGS. 15A to 15D are graphs illustrating the aberrations of the endoscope optical system according to the example 7 of the invention.

FIG. 14 is a cross sectional view illustrating the arrangement of the optical components including the endoscope optical system 100 according to the example 7. As shown in FIG. 14, the endoscope optical system 100 according to the example 7 has the same number of optical components as that of the endoscope optical system 100 according to the example 1. FIGS. 15A to 15D are aberration diagrams (the spherical aberration, the longitudinal chromatic aberration, the chromatic difference of magnification, the astigmatism and the distortion) of the endoscope optical system 100 according to the example 7. Table 13 shows the numeric configuration of the optical components including the endoscope optical system 100 according to the example 7. Table 14 shows the specifications of the endoscope optical system 100 according to the example 7.

TABLE 13

| Surface No. | R | D | N(d) | νd |
|---|---|---|---|---|
| 1 | INFINITY | 0.687 | 1.88300 | 40.8 |
| 2 | 1.071 | 0.210 | | |
| 3 | 1.947 | 0.981 | 1.84666 | 23.8 |
| 4 | INFINITY | 0.000 | | |
| 5(aperture stop) | INFINITY | 0.095 | | |
| 6 | −1.397 | 0.846 | 1.88300 | 40.8 |
| 7 | −1.007 | 0.354 | | |
| 8 | −5.635 | 0.317 | 1.92286 | 18.9 |
| 9 | 2.355 | 1.586 | 1.88300 | 40.8 |
| 10 | −2.347 | 1.470 | | |
| 11 | INFINITY | 1.000 | 1.51633 | 64.1 |
| 12 | INFINITY | — | | |

TABLE 14

| | |
|---|---|
| F number | 11.10 |
| Magnification | −0.064 |
| Half Field Angle | 69.000 |
| Image Height | 1.310 |
| Back Focus BF | 0.000 |
| Overall Length of Lens | 7.550 |
| Focal Length f | 1.322 |
| Exit Pupil Distance EX | −12.199 |
| Focal Length $f_1$ of Front Group G1 | −3.182 |
| Focal Length $f_2$ of Rear Group G2 | 1.669 |
| Focal Length $f_{21}$ of Positive Lens L3 | 2.025 |
| Focal Length $f_c$ of Cemented Lens L4 | 3.806 |

Comparative Example 1

Figure 16:
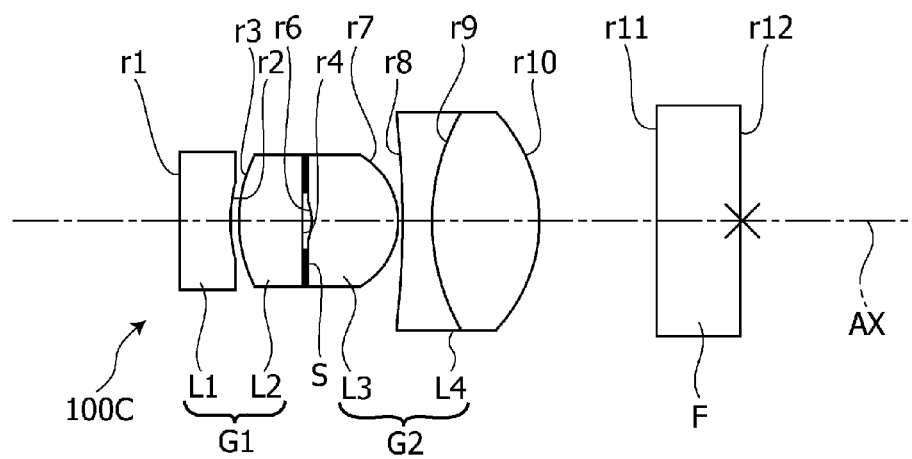
FIG. 16 is a cross sectional view of an endoscope optical system and optical components located on the downstream side of the endoscope optical system according to comparative example 1.

FIG. 16 is a cross sectional view illustrating the arrangement of the optical components including an endoscope optical system 100C according to the comparative example 1. As shown in FIG. 16, the endoscope optical system 100C according to the comparative example 1 has the same number of optical components as that of the endoscope optical system 100 according to the example 1. FIGS. 17A to 17D are aberration diagrams (the spherical aberration, the longitudinal chromatic aberration, the chromatic difference of magnification, the astigmatism and the distortion) of the endoscope optical system 100C according to the comparative example 1. Table 15 shows the numeric configuration of the optical components including the endoscope optical system 100C according to the comparative example 1. Table 16 shows the specifications of the endoscope optical system 100C according to the comparative example 1.

TABLE 15

| Surface No. | R | D | N(d) | vd |
|---|---|---|---|---|
| 1 | INFINITY | 0.609 | 1.88300 | 40.8 |
| 2 | 1.793 | 0.102 | | |
| 3 | 1.762 | 0.812 | 1.84666 | 23.8 |
| 4 | INFINITY | 0.000 | | |
| 5(aperture stop) | INFINITY | 0.060 | | |
| 6 | −0.722 | 1.039 | 1.88300 | 40.8 |
| 7 | −0.928 | 0.051 | | |
| 8 | −11.759 | 0.355 | 1.92286 | 18.9 |
| 9 | 2.672 | 1.288 | 1.77250 | 49.6 |
| 10 | −1.941 | 1.410 | | |
| 11 | INFINITY | 1.000 | 1.51680 | 64.2 |
| 12 | INFINITY | — | | |

TABLE 16

| | |
|---|---|
| F number | 7.500 |
| Magnification | −0.081 |
| Half Field Angle | 74.400 |
| Image Height | 1.300 |
| Back Focus BF | 0.020 |
| Overall Length of Lens | 6.750 |
| Focal Length f | 1.279 |
| Exit Pupil Distance EX | −15.998 |
| Focal Length $f_1$ of Front Group G1 | 83.156 |
| Focal Length $f_2$ of Rear Group G2 | 1.338 |
| Focal Length $f_{21}$ of Positive Lens L3 | 2.703 |
| Focal Length $f_c$ of Cemented Lens L4 | 3.254 |

Comparative Example 2

Figure 18:
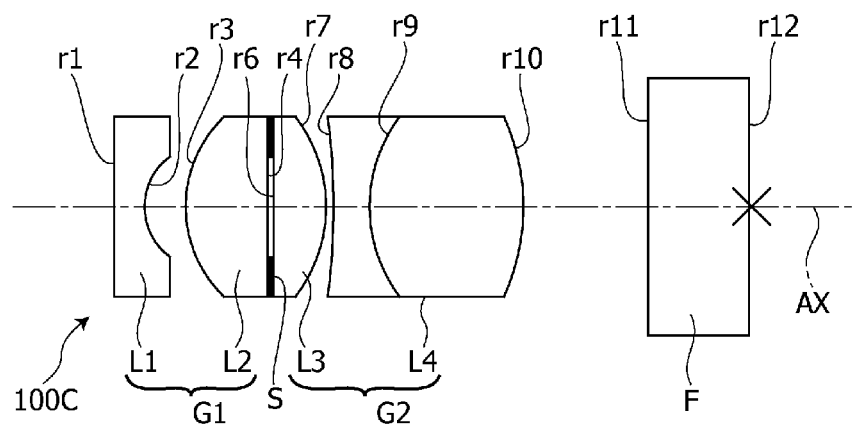
FIG. 18 is a cross sectional view of an endoscope optical system and optical components located on the downstream side of the endoscope optical system according to comparative example 2.
Figure 19:
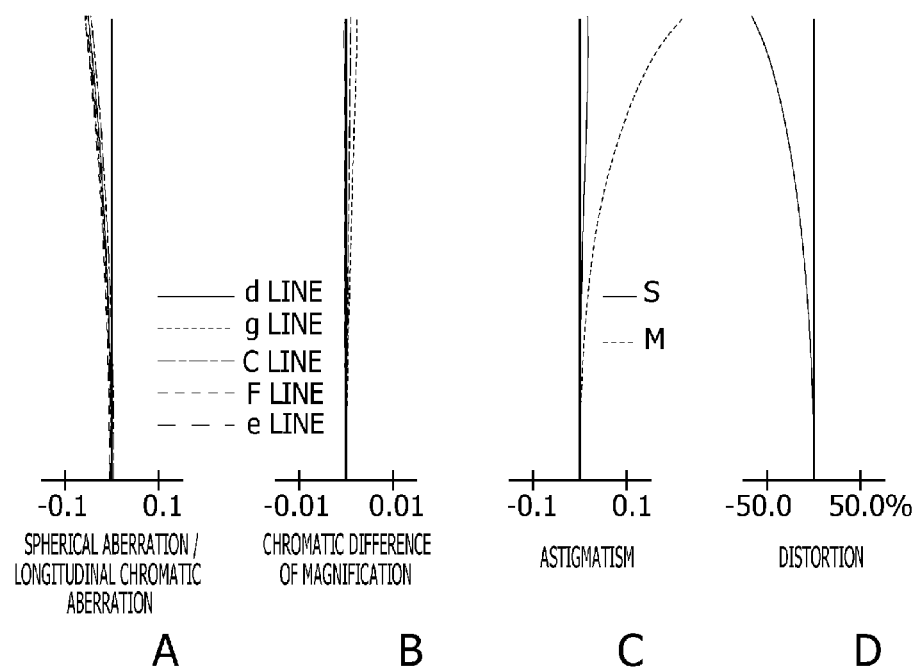
FIGS. 19A to 19D are graphs illustrating the aberrations of the endoscope optical system according to the comparative example 2.

FIG. 18 is a cross sectional view illustrating the arrangement of the optical components including the endoscope optical system 100C according to the comparative example 2. As shown in FIG. 18, the endoscope optical system 100C according to the comparative example 2 has the same number of optical components as that of the endoscope optical system 100 according to the example 1. FIGS. 19A to 19D are aberration diagrams (the spherical aberration, the longitudinal chromatic aberration, the chromatic difference of magnification, the astigmatism and the distortion) of the endoscope optical system 100C according to the comparative example 2. Table 17 shows the numeric configuration of the optical components including the endoscope optical system 100C according to the comparative example 2. Table 18 shows the specifications of the endoscope optical system 100C according to the comparative example 2.

TABLE 17

| Surface No. | R | D | N(d) | vd |
|---|---|---|---|---|
| 1 | INFINITY | 0.305 | 1.88300 | 40.8 |
| 2 | 0.626 | 0.406 | | |
| 3 | 1.260 | 0.813 | 1.84666 | 23.8 |
| 4 | INFINITY | 0.000 | | |
| 5(aperture stop) | INFINITY | 0.061 | | |
| 6 | −30.139 | 0.516 | 1.88300 | 40.8 |
| 7 | −1.487 | 0.074 | | |
| 8 | −7.060 | 0.355 | 1.92286 | 18.9 |
| 9 | 1.508 | 1.524 | 1.77250 | 49.6 |
| 10 | −2.196 | 1.233 | | |
| 11 | INFINITY | 1.000 | 1.51680 | 64.2 |
| 12 | INFINITY | — | | |

TABLE 18

| | |
|---|---|
| F number | 7.700 |
| Magnification | −0.081 |
| Half Field Angle | 72.300 |
| Image Height | 1.300 |
| Back Focus BF | 0.020 |
| Overall Length of Lens | 6.310 |
| Focal Length f | 1.235 |
| Exit Pupil Distance EX | −4.950 |
| Focal Length $f_1$ of Front Group G1 | −2.836 |
| Focal Length $f_2$ of Rear Group G2 | 1.791 |
| Focal Length $f_{21}$ of Positive Lens L3 | 1.757 |
| Focal Length $f_c$ of Cemented Lens L4 | 5.056 |

Comparison

The following Table 19 shows values of the conditions (1) to (8) for each of the above described examples 1 to 7 and the comparative examples 1 and 2.

TABLE 19

| CONDITION | EXAMPLE 1 | EXAMPLE 2 | EXAMPLE 3 | EXAMPLE 4 | EXAMPLE 5 |
|---|---|---|---|---|---|
| (1) | −6.859 | −7.865 | −6.831 | −7.525 | −6.817 |
| (2) | 1.292 | 1.326 | 1.305 | 1.318 | 1.255 |
| (3) | 2.327 | 2.057 | 2.296 | 2.978 | 2.743 |
| (4) | −1.339 | −1.209 | −1.314 | −1.480 | −1.302 |
| (5) | −0.177 | −0.214 | −0.091 | 0.000 | −0.263 |
| (6) | −5.661 | −4.669 | −10.934 | −∞ | −3.808 |
| (7) | 1.432 | 1.605 | 1.469 | 1.469 | 1.431 |
| (8) | −0.371 | −0.581 | −0.645 | −0.439 | −0.401 |

| CONDITION | EXAMPLE 6 | EXAMPLE 7 | COMPARATIVE EXAMPLE 1 | COMPARATIVE EXAMPLE 2 |
|---|---|---|---|---|
| (1) | −6.718 | −9.231 | −12.505 | −4.007 |
| (2) | 1.233 | 1.263 | 1.046 | 1.450 |
| (3) | 2.749 | 2.280 | 2.432 | 2.824 |
| (4) | −1.595 | −2.408 | 65.001 | −2.296 |
| (5) | −0.034 | −0.416 | −0.165 | −0.311 |
| (6) | −29.741 | −2.402 | −6.057 | −3.214 |

TABLE 19-continued

| | | | | |
|---|---|---|---|---|
| (7) | 1.737 | 1.532 | 2.113 | 1.423 |
| (8) | −0.333 | −0.946 | −1.771 | −0.041 |

Figure 17:
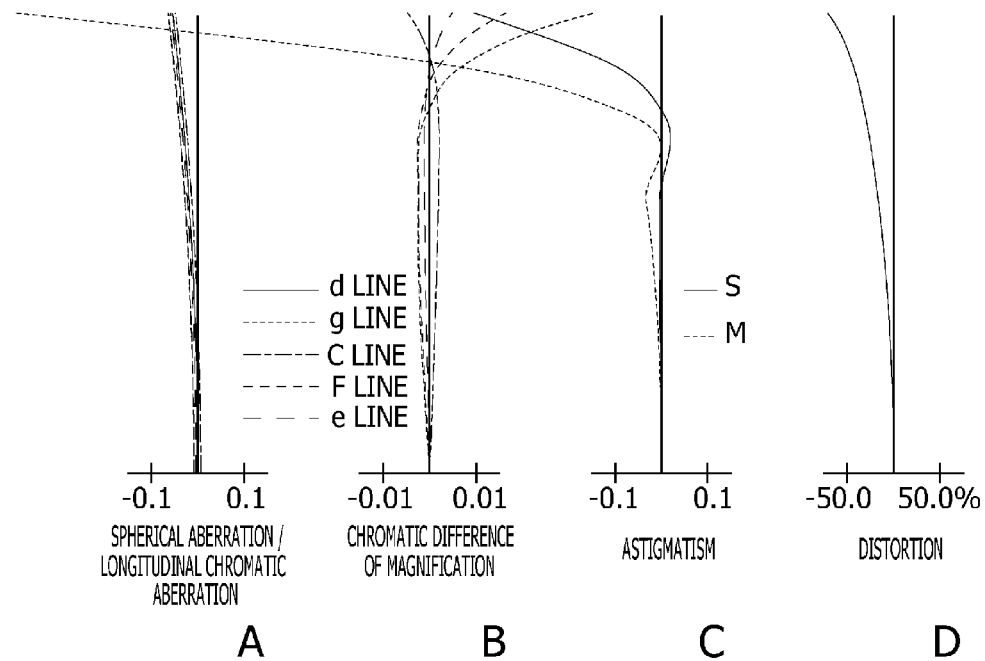
FIGS. 17A to 17D are graphs illustrating the aberrations of the endoscope optical system according to the comparative example 1.

As shown in Table 19, the endoscope optical system 100C according to each of the comparative examples 1 and 2 does not satisfy the conditions (1) and (2). Since the lens diameter of the cemented lens L4 of the endoscope optical system 100C according to the comparative example 1 is large as shown in FIG. 16 or 17, the endoscope optical system 100C according to the comparative example 1 is not suitable for installation in the tip part 12, and causes a large amount of astigmatism due to the curvature of field (in particular, the curvature of the meridional image plane). Since the exit pupil distance EX of the endoscope optical system 100C according to the comparative example 2 is short as shown in Table 18, the shortage of the peripheral light amount due to shading is large as in the case of the endoscope optical system described in each of the patent documents #1 to #6.

By contrast, the endoscope optical system 100 according to each of the examples 1 to 7 satisfies the conditions (1) and (2) simultaneously as shown in Table 19. Therefore, the endoscope optical system 100 according to each of the examples 1 to 7 can be configured to reduce the size to be suitable for installation in the tip part 12 having the small outer diameter while securing the optical performance required for observation of a fine structure in a body cavity. In particular, since the incident angle of light with respect to the image plane can be suppressed by securing the exit pupil distance EX, the shortage of the peripheral light amount due to shading is small even when the image is formed on the image pick-up device having a large number of pixels, such as a megapixel.

The endoscope optical system 100 according to each of the examples 1 to 7 further satisfies the conditions (3) to (8). Therefore, the endoscope optical system 100 according to each of the examples 1 to 7 is also able to achieve the advantages which are described above in relation to the conditions (3) to (8), in addition to the advantages brought by satisfying the conditions (1) and (2).

The foregoing is the explanation about the embodiment of the invention. It should be noted that the present invention is not limited to the above described configurations, and various types of variations can be made within the scope of the technical concept of the invention.

The invention claimed is:

1. An endoscope optical system, comprising:
a front group; and
a rear group,
the front group and the rear group being arranged in this order from an object side such that an aperture stop is arranged between the front group and the rear group, wherein:
the front group comprises a negative lens and a positive lens arranged in this order from the object side;
the rear group comprises a positive lens and a cemented lens arranged in this order from the object side; and
when f (unit: mm) denotes a focal length of an entire endoscope optical system, EX (unit: mm) denotes a distance (which takes a minus sign on the object side with respect to an image plane) from the image plane to an exit pupil, and $f_2$ (unit: mm) denotes a focal length of the rear group, the endoscope optical system satisfies conditions:

$$-10 < EX/f < -6 \quad (1),$$

and $$1.15 < f_2/f < 1.35 \quad (2).$$

2. The endoscope optical system according to claim 1, wherein when $f_c$ (unit: mm) denotes a focal length of the cemented lens, the endoscope optical systems satisfies a condition:

$$2 < f_c/f_2 < 3.2 \quad (3).$$

3. The endoscope optical system according to claim 1, wherein when $f_1$ (unit: mm) denotes a focal length of the front group, the endoscope optical system satisfies a condition:

$$-2.5 < f_1/f < -1.2 \quad (4).$$

4. The endoscope optical system according to claim 1, wherein when $R_8$ (unit: mm) denotes a radius of curvature of an object side surface of the cemented lens and $R_{10}$ (unit: mm) denotes a radius of curvature of an image side surface of the cemented lens, the endoscope optical system satisfies a condition:

$$-0.5 < R_{10}/|R_8| \leq 0 \quad (5).$$

5. The endoscope optical system according to claim 1, wherein when $R_8$ (unit: mm) denotes a radius of curvature of an object side surface of the cemented lens and $R_{10}$ (unit: mm) denotes a radius of curvature of an image side surface of the cemented lens, the endoscope optical system satisfies a condition:

$$|R_8|/R_{10} < -2 \quad (6).$$

6. The endoscope optical system according to claim 1, wherein:
the positive lens of the rear group is a positive meniscus lens having a concave surface facing the object side; and
when $f_{21}$ (unit: mm) denotes a focal length of the positive lens of the rear group, and $R_6$ (unit: mm) denotes a radius of curvature of an object side surface of the positive lens of the rear group, the endoscope optical system satisfies conditions:

$$1.3 < f_{21}/f < 1.8 \quad (7),$$

and $$-1 < f/R_6 < -0.3 \quad (8).$$

7. An endoscope, comprising:
a flexible insertion tube; and
an endoscope optical system according to claim 1 provided in a tip part of the flexible insertion tube.

* * * * *